(12) United States Patent
Atwell

(10) Patent No.: US 11,432,865 B2
(45) Date of Patent: Sep. 6, 2022

(54) METHOD OF INSERTING AN ELECTROSURGICAL INSTRUMENT INTO AN ENDOSCOPE IN AN APPARATUS FOR IONISABLE GAS COAGULATION AND OPERATING THE ELECTROSURGICAL INSTRUMENT IN THE ENDOSCOPE AFTER INSERTION

(71) Applicant: GYRUS MEDICAL LIMITED, Cardiff (GB)

(72) Inventor: Tony Atwell, Newport (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 641 days.

(21) Appl. No.: 16/251,709

(22) Filed: Jan. 18, 2019

(65) Prior Publication Data
US 2019/0231410 A1 Aug. 1, 2019

Related U.S. Application Data

(60) Provisional application No. 62/622,497, filed on Jan. 26, 2018.

(51) Int. Cl.
*A61N 1/44* (2006.01)
*A61B 18/04* (2006.01)
(Continued)

(52) U.S. Cl.
CPC ........ *A61B 18/042* (2013.01); *A61B 18/1206* (2013.01); *A61B 18/14* (2013.01);
(Continued)

(58) Field of Classification Search
CPC ... A61B 18/042; A61B 18/14; A61B 18/1206; A61B 2018/00982; A61B 2018/00863;
(Continued)

(56) References Cited

U.S. PATENT DOCUMENTS 4,040,426 A 8/1977 Morrison, Jr.
4,781,175 A * 11/1988 McGreevy ........... A61B 18/042
219/121.5
(Continued)

FOREIGN PATENT DOCUMENTS

CN 107518942 A * 12/2017
DE 102004033975 A1 * 1/2006 ........... A61B 18/042
(Continued)

*Primary Examiner* — Daniel W Fowler
(74) *Attorney, Agent, or Firm* — Oliff PLC

(57) ABSTRACT

A method of operating an electrosurgical apparatus for coagulating tissue comprises inserting the electrosurgical instrument into an endoscope, and activating a source to supply ionisable gas to the electrosurgical instrument at a flow rate of less than a predetermined threshold flow rate while the electrosurgical instrument is being inserted into the endoscope. Once the electrosurgical instrument has been fully inserted into the endoscope, the source is activated to supply ionisable gas to the electrosurgical instrument at a flow rate of greater than the predetermined threshold flow rate. Finally, high frequency energy is supplied from an electrosurgical generator to the electrosurgical instrument, in order to ionise the ionisable gas flowing to the electrosurgical instrument.

9 Claims, 3 Drawing Sheets

Figure 1:
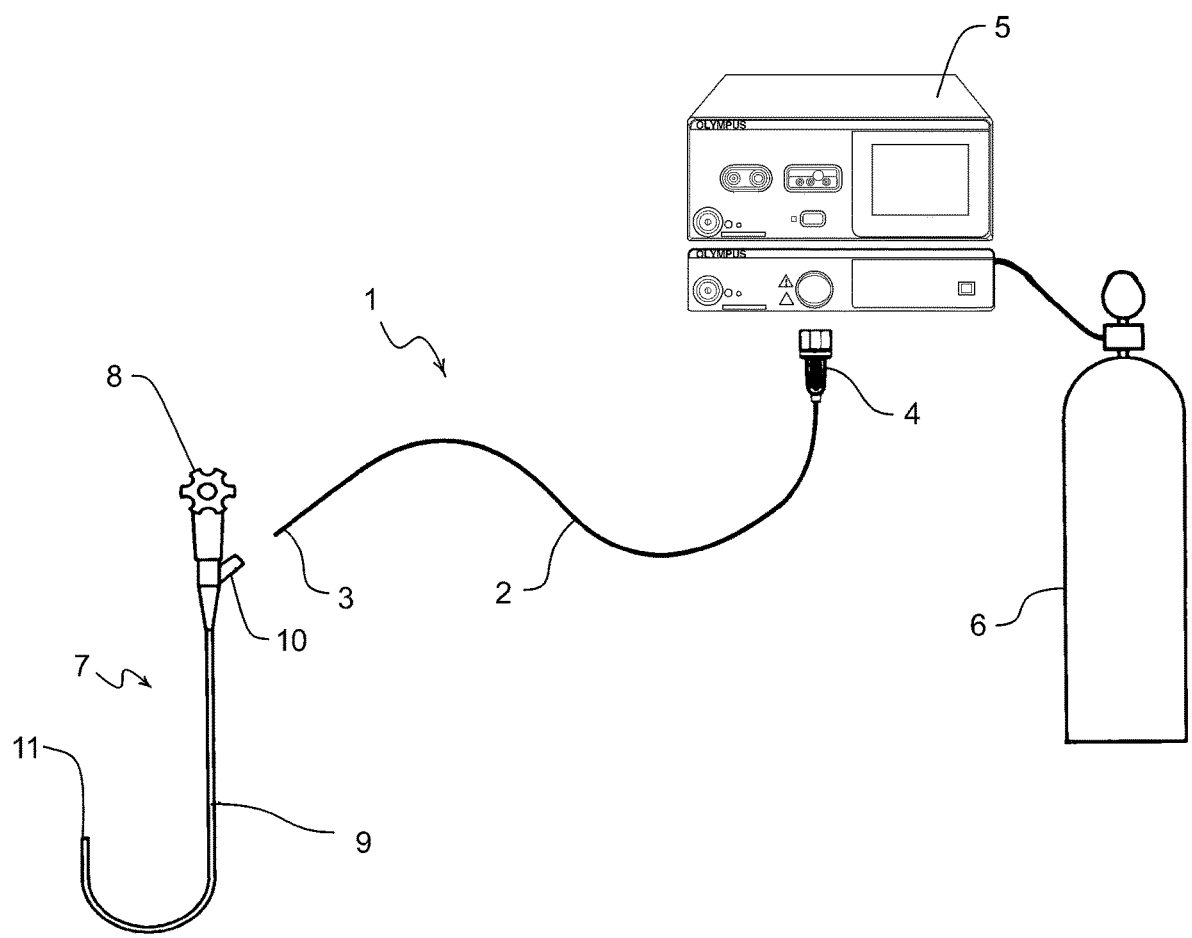

(51) Int. Cl.
*A61B 18/14* (2006.01)
*A61B 18/12* (2006.01)
*A61B 17/00* (2006.01)
*A61B 18/00* (2006.01)

(52) U.S. Cl.
CPC ............... *A61B 2017/00296* (2013.01); *A61B 2017/00469* (2013.01); *A61B 2018/00583* (2013.01); *A61B 2018/00589* (2013.01); *A61B 2018/00863* (2013.01); *A61B 2018/00982* (2013.01); *A61B 2018/1495* (2013.01)

(58) Field of Classification Search
CPC ........... A61B 2018/00583; A61B 2017/00296; A61B 2017/00469; A61B 2018/1495; A61B 2018/00589
See application file for complete search history.

(56) References Cited

U.S. PATENT DOCUMENTS

| | | | |
|---|---|---|---|
| 5,207,675 A * | 5/1993 | Canady | A61B 18/042 606/37 |
| 5,720,745 A | 2/1998 | Farin et al. | |
| 6,039,736 A | 3/2000 | Platt, Jr. | |
| 6,197,026 B1 | 3/2001 | Farin et al. | |
| 6,206,878 B1 * | 3/2001 | Bishop | A61B 18/042 219/121.55 |
| 7,648,503 B2 * | 1/2010 | Podhajsky | A61B 18/042 606/49 |
| 8,157,795 B2 * | 4/2012 | Sartor | A61B 18/042 606/41 |
| 8,221,404 B2 * | 7/2012 | Truckai | A61B 18/042 606/32 |
| 8,287,530 B2 * | 10/2012 | Morris | A61B 18/042 606/37 |
| 8,382,753 B2 * | 2/2013 | Truckai | A61B 18/1477 606/41 |
| 9,089,319 B2 * | 7/2015 | Suslov | A61B 18/042 606/13 |

FOREIGN PATENT DOCUMENTS

| | | | |
|---|---|---|---|
| DE | 10129685 B4 * | 9/2007 | ........... A61B 18/042 |
| JP | 2001128987 A * | 5/2001 | ........... A61B 18/042 |

* cited by examiner

METHOD OF INSERTING AN ELECTROSURGICAL INSTRUMENT INTO AN ENDOSCOPE IN AN APPARATUS FOR IONISABLE GAS COAGULATION AND OPERATING THE ELECTROSURGICAL INSTRUMENT IN THE ENDOSCOPE AFTER INSERTION

FIELD

This invention relates to an electrosurgical method and in particular to the non-contact coagulation of tissue using an ionisable gas such as argon.

BACKGROUND

Argon beam coagulators have been known for many years, and examples are given in U.S. Pat. Nos. 4,040,426, 5,720,745, 6,039,736 and 6,197,026. The first example is an end-effect instrument, in which the ionised gas exits through the end of the instrument, while the latter two examples are directed at side-effect instruments, in which the ionised gas exits the instrument though an aperture in the side of the instrument. Such instruments are often referred to as APC instruments (Argon Plasma Coagulation).

APC instruments are often used in endoluminal procedures in which the length of the instrument is many times its diameter. In such situations the instrument is deployed through an endoscope, which can be 1 m or more in length. It is often the case that fluids present within the endoscope can enter the APC instrument and make it difficult for the instrument to produce the ionised gas as required. The present invention attempts to provide an improved method in this regard.

SUMMARY

Accordingly, a method of operating an apparatus for ionisable gas coagulation is provided, the apparatus comprising at least an endoscope, an electrosurgical instrument capable of being inserted through the endoscope, a source for supplying ionisable gas to said electrosurgical instrument, and an electrosurgical generator for supplying high frequency energy to said electrosurgical instrument, and wherein the method comprises the following steps:
  a) inserting the electrosurgical instrument into the endoscope;
  b) activating the source to supply ionisable gas to the electrosurgical instrument at a flow rate of less than a predetermined threshold flow rate while the electrosurgical instrument is being inserted into the endoscope;
  c) activating the source to supply ionisable gas to the electrosurgical instrument at a flow rate of greater than the predetermined threshold flow rate when the electrosurgical instrument has been fully inserted into the endoscope; and
  d) supplying high frequency energy from the electrosurgical generator to said electrosurgical instrument, in order to ionise the ionisable gas flowing to the electrosurgical instrument in step c.

The supply of gas at the relatively low flow rate of less than the predetermined threshold flow rate is sufficient to prevent the ingress of fluids to the instrument while the instrument is being inserted into the endoscope. However, this relatively low flow rate is not sufficient to cause any damage to the endoscope, or make it difficult for the instrument to be inserted. The predetermined threshold flow rate is conveniently between 0.2 and 0.75 litres per minute, and preferably between 0.25 and 0.5 litres per minute. Typically, in step b, the source is activated to supply ionisable gas to the electrosurgical instrument at a flow rate of less than 0.15 litres per minute.

Once the electrosurgical instrument has been fully inserted into the endoscope, the ionisable gas is supplied to the instrument at a flow rate greater than the predetermined threshold flow rate. Conveniently, in step c, the source is activated to supply ionisable gas to the electrosurgical instrument at a flow rate of greater than 0.3 litres per minute, typically greater than 0.6 litres per minute, and conceivably greater than 1.6 litres per minute.

During the insertion of the instrument into the endoscope, the source is conceivably activated to supply ionisable gas to the electrosurgical instrument in pulses. Alternately or additionally, when the electrosurgical instrument has been fully inserted into the endoscope, the source is activated to supply ionisable gas to the electrosurgical instrument in pulses. In this way, the gas can be supplied in pulses either during the insertion of the instrument into the endoscope, or during activation of the instrument, or both.

DRAWINGS

Figure 2:
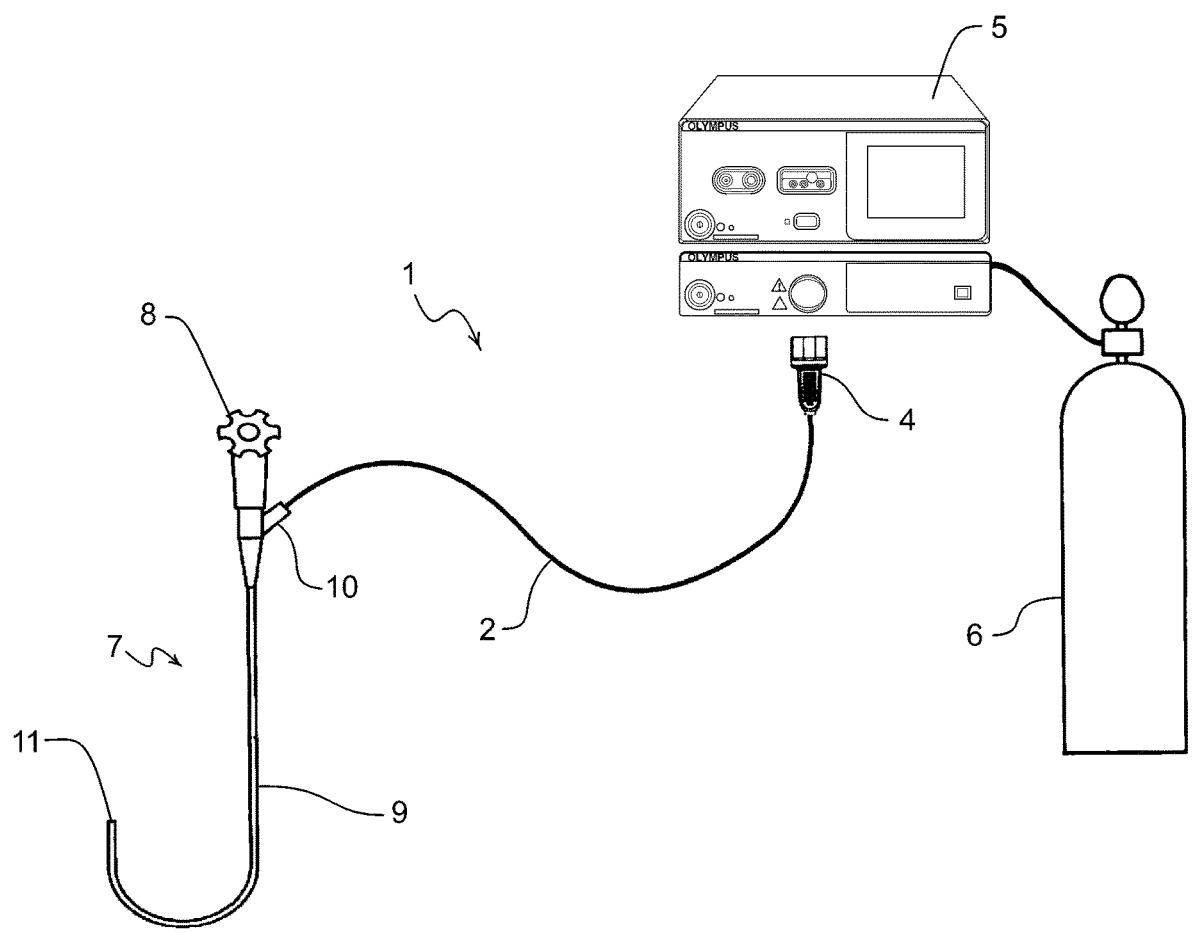
Figure 3:
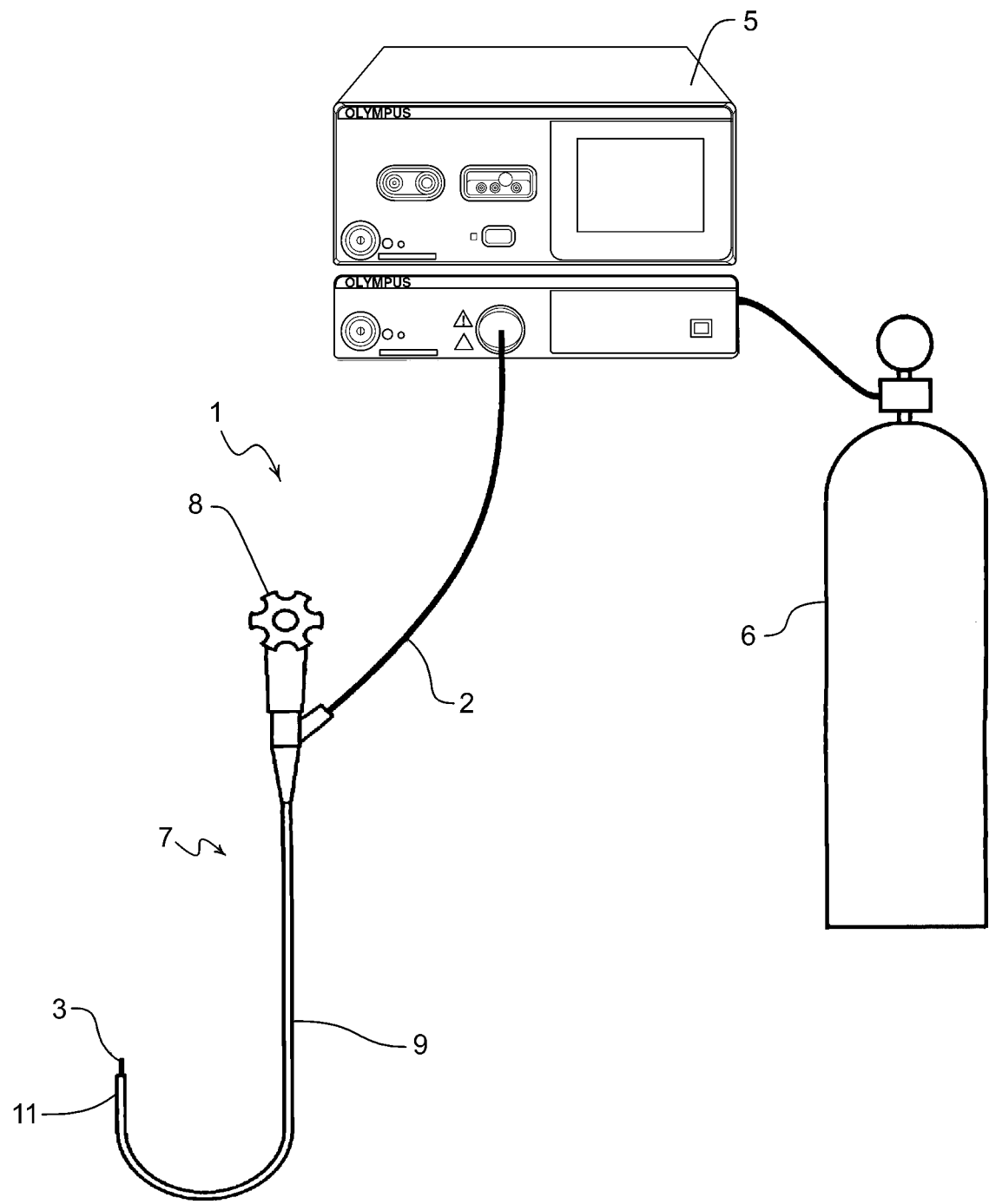

The invention will now be further described, by way of example only, with reference to the accompanying drawings, in which:

FIG. 1 is a schematic view of an electrosurgical system employing an APC instrument, FIG. 2 is a schematic view of the electrosurgical system of FIG. 1, showing the instrument being inserted into an endoscope, and FIG. 3 is a schematic view of the electrosurgical system of FIG. 1, showing the instrument fully inserted into the endoscope.

Corresponding reference numerals indicate corresponding parts throughout the drawings.

DETAILED DESCRIPTION

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

Referring to FIG. 1, an APC system comprises an APC probe shown generally at 1, and comprising a flexible elongate shaft 2 having a distal tip 3 and a plug 4 at the proximal end of the shaft. The plug 4 connects the probe 1 to an electrosurgical generator 5, the generator 5 also including a cylinder 6 of argon gas. The argon gas is supplied through the cable shaft 2 along with electrosurgical energy to ionise the gas when required. The system is completed by an endoscope 7, the endoscope including an optics port 8 and an elongate sheath 9. The sheath has a proximal port 10 into which the probe 1 can be inserted, and a distal opening 11 from which the tip of the probe can emerge.

FIG. 2 shows the probe 1 ready for insertion into the endoscope 7. The plug 4 is connected to the generator 5, and the endoscope 7 is inserted into the patient such that the distal end of the sheath 9 is located at the surgical site which is requiring treatment. The distal tip 3 of the probe is then inserted into the proximal port 10 of the endoscope. As the probe is pushed through the sheath 9 to emerge through the distal opening 11, argon gas is supplied at a flow rate of 0.1 litres per minute. This flow of argon gas prevents any fluids present within the sheath 9 from entering the probe 1, which typically has an open distal end. However, the flow of argon gas is at a relatively low flow rate, such that it does not damage either the sheath 9 or the tissue at the surgical site.

FIG. 3 shows the probe 1 fully inserted in the endoscope 7, with the tip 3 of the probe slightly extending from the distal opening 11 of the sheath 9. The generator 5 is then activated firstly to cause the supply of argon gas through the probe 1 at a higher flow rate, typically 0.3 litres per minute for the smallest diameter probes, 0.8 litres per minute for medium diameter probes, and 1.6 litres per minute for the largest diameter probes. The generator then supplies high frequency energy to an electrode (not shown) at the tip 3 of the probe, such that the argon gas is ionised as it emerges from the probe 1. This ionised argon gas impinges on tissue, thereby coagulating it, as is well known in APC instrument.

The supply of argon gas at a relatively low flow rate while the probe 1 is being inserted into the endoscope 7 is the improvement offered by the present invention. It prevents fluids being drawn into the probe while it is being inserted, which can potentially inhibit the subsequent ionisation of the argon gas by the probe. The argon gas may be supplied to the probe in pulses, either during insertion and/or during subsequent activation of the electrode to ionise the gas.

The foregoing description has been provided for purposes of illustration and description. It is not intended to be exhaustive or to limit the disclosure. Individual elements or features of a particular configuration are generally not limited to that particular configuration, but, where applicable, are interchangeable and can be used in a selected configuration, even if not specifically shown or described. The same may also be varied in many ways. Such variations are not to be regarded as a departure from the disclosure, and all such modifications are intended to be included within the scope of the disclosure.

What is claimed is:

1. A method of operating an apparatus for ionisable gas coagulation, the apparatus comprising at least an endoscope, an electrosurgical instrument capable of being inserted through the endoscope, a source for supplying ionisable gas to said electrosurgical instrument, and an electrosurgical generator for supplying high frequency energy to said electrosurgical instrument, and wherein the method comprises the following steps:
    a) inserting the electrosurgical instrument into the endoscope;
    b) activating the source to supply ionisable gas to the electrosurgical instrument at a flow rate of less than a predetermined threshold flow rate while the electrosurgical instrument is being inserted into the endoscope;
    c) activating the source to supply ionisable gas to the electrosurgical instrument at a flow rate of greater than the predetermined threshold flow rate when the electrosurgical instrument has been fully inserted into the endoscope; and
    d) supplying high frequency energy from the electrosurgical generator to said electrosurgical instrument, in order to ionise the ionisable gas flowing to the electrosurgical instrument in step c.

2. A method according to claim 1, wherein the predetermined threshold flow rate is between 0.2 and 0.75 litres per minute.

3. A method according to claim 2, wherein the predetermined threshold flow rate is between 0.25 and 0.5 litres per minute.

4. A method according to claim 1, wherein in step b, the source is activated to supply ionisable gas to the electrosurgical instrument at a flow rate of less than 0.15 litres per minute.

5. A method according to claim 1, wherein in step c, the source is activated to supply ionisable gas to the electrosurgical instrument at a flow rate of greater than 0.3 litres per minute.

6. A method according to claim 5, wherein in step c, the source is activated to supply ionisable gas to the electrosurgical instrument at a flow rate of greater than 0.8 litres per minute.

7. A method according to claim 6, wherein in step c, the source is activated to supply ionisable gas to the electrosurgical instrument at a flow rate of greater than 1.6 litres per minute.

8. A method according to claim 1, wherein in step b, the source is activated to supply ionisable gas to the electrosurgical instrument in pulses.

9. A method according to claim 1, wherein in step c, the source is activated to supply ionisable gas to the electrosurgical instrument in pulses.

* * * * *